US009125984B2

(12) United States Patent \
Friebe et al.

(10) Patent No.: US 9,125,984 B2 \
(45) Date of Patent: Sep. 8, 2015

(54) HYDRAULIC INJECTION SYSTEM AND INJECTION METHOD

(75) Inventors: Michael H. Friebe, Recklinghausen (DE); Paul Willi Coenen, Titz-Rödingen (DE); Ralf Jauster, Stolberg (DE)

(73) Assignee: ACIST Medical Systems, Inc., Eden Prairie, MN (US)

( * ) Notice: Subject to any disclaimer, the term of this patent is extended or adjusted under 35 U.S.C. 154(b) by 2595 days.

(21) Appl. No.: 12/444,134

(22) PCT Filed: Jun. 23, 2005

(86) PCT No.: PCT/EP2005/006809 \
§ 371 (c)(1), \
(2), (4) Date: Oct. 15, 2009

(87) PCT Pub. No.: WO2006/000415 \
PCT Pub. Date: Jan. 5, 2006

(65) Prior Publication Data \
US 2010/0042068 A1    Feb. 18, 2010

(30) Foreign Application Priority Data

Jun. 24, 2004    (DE) .................. 10 2004 030 690

(51) Int. Cl. \
*A61M 31/00*    (2006.01) \
*A61M 5/145*    (2006.01) \
*A61M 5/00*    (2006.01)

(52) U.S. Cl. \
CPC ........... *A61M 5/14526* (2013.01); *A61M 5/007* (2013.01); *A61M 2005/14513* (2013.01); *A61M 2205/3561* (2013.01)

(58) Field of Classification Search \
CPC .................. A61M 2005/14513; A61M 5/007; A61M 5/14216; A61M 5/14546 \
USPC ............... 604/65–67, 151–155, 890.1–892.1, 604/131; 600/420, 431–435 \
See application file for complete search history.

(56) References Cited

U.S. PATENT DOCUMENTS 4,250,887 A    2/1981    Dardik et al. \
5,494,036 A    2/1996    Uber, III et al. \
(Continued)

FOREIGN PATENT DOCUMENTS

| | | |
|---|---|---|
| JP | 07178169 | 7/1995 |
| JP | 07-204176 | 8/1995 |
| JP | 2000-070365 | 3/2000 |

OTHER PUBLICATIONS

Japanese Office Action from corresponding Japanese Application No. 2007-517205 (7 pages). \
International Search Report and International Report on Patentability for PCT/EP2005/006809 filed Jun. 23, 2005. \
(Continued)

*Primary Examiner* — Phillip Gray \
(74) *Attorney, Agent, or Firm* — Fredrikson & Byron, P.A.

(57) ABSTRACT

Disclosed is an injection system (1) for injecting liquids within a strong magnetic field, an alternating magnetic field, and/or a high-frequency electric field to be used with a technical medical system. Said injection system comprises a space (2) that is shielded from electromagnetic fields with the aid of a shield, an injection device (6) by means of which liquid to be injected can be dispensed to a patient (23), a driving mechanism for the injection device (6), by means of which at least one conveying element (11, 12) can be displaced for injection purposes, and a control and monitoring unit (8) which is located outside said space (2). The inventive injection system prevents interfering electromagnetic fields from being created exclusively by the fact that a hydraulic driving mechanism (10) is provided whose at least one hydraulic conduit (13, 14, 15, 16) is guided out of the space (2) to a pressure generating unit (71, 72, 73, 74).

15 Claims, 2 Drawing Sheets

(56) References Cited

U.S. PATENT DOCUMENTS

| | | |
|---|---|---|
| 6,198,287 B1 | 3/2001 | Heiserholt et al. |
| 6,216,029 B1 * | 4/2001 | Paltieli .......................... 600/427 |
| 6,575,965 B1 * | 6/2003 | Benett et al. ..................... 606/15 |
| 7,512,434 B2 | 3/2009 | Staats et al. |
| 2002/0115933 A1 * | 8/2002 | Duchon et al. ................. 600/432 |

OTHER PUBLICATIONS

Brummett, M.D., David; Fidler, M.D., Jeff; Stark, M.D. David; "Power Injectors for MRI", Applied Radiology, The Journal of Practial Medical Imaging and Management; May 1999, vol. 28, No. 5; pp. 15-20.

* cited by examiner

HYDRAULIC INJECTION SYSTEM AND INJECTION METHOD

CROSS REFERENCE TO RELATED APPLICATIONS

This application is a national stage application filed under 35 U.S.C. 371 of International Application No. PCT/EP2005/006809, filed Jun. 23, 2005, which claims priority to German Application No. 10 2004 030 690.7, filed Jun. 24, 2004.

FIELD AND BACKGROUND OF THE INVENTION

The invention relates to an injection system for injecting liquids within a strong magnetic field, an alternating magnetic field and/or a high-frequency electric field, for use with a medical technical system, comprising a room which is shielded from electromagnetic fields by means of a shield, an injection device, by means of which liquid to be injected can be dispensed to a patient, a drive device of the injection device, by means of which at least one conveying element can be displaced, and a control and monitoring unit which is arranged outside the room.

Such injection systems are used in particular in the field of magnetic resonance imaging (MRI), in order by injection of a contrast agent to obtain tomograms of internal organs of a patient that allow diagnosis. It is generally known that MRI systems have to be isolated in the best possible way from external electromagnetic fields, so as to obtain an optimal image quality or tomogram quality using the MRI system. This is achieved by shielding from such (sometimes unpredictable) sources of electromagnetic fields the entire room in which the MRI system is located, by means of a copper shield or by means of conductive mesh material. In order to take full advantage of such a shielded room, attempts are also made to shield from the MRI system the injection system and method for injecting liquids, in particular contrast media and saline solution for use with an MRI system, or to move at least part of said system and method outside, since the injection system and method may themselves be sources of electromagnetic fields and may have an adverse effect on image quality.

An injection system of the type described in the introduction is known in general for example from U.S. Pat. No. 5,494,036 A. By extensive design measures, this system prevents the image quality from being too greatly affected by electromagnetic radiation.

The injection device disclosed in U.S. Pat. No. 5,494,036 A consists of a drive device in the form of two DC electric motors and two cylinder/piston units in the form of syringes. Via a coupling device, which may optionally also be configured in a hydraulic manner but in particular is formed by two drive spindles (flexible drive shaft), the pistons of the syringes are moved forwards and backwards independently of one another by means of the drive spindles. Here, a rotational movement of a threaded and axially fixed drive element of the respective electric motor is converted into a linear forward and backward movement of the piston in the syringe. As a result of the forward and backward movement of the syringe piston, contrast agent and saline solution can be taken up and subsequently dispensed. The syringes can be connected via a Y-shaped adapter and intermediate hoses to a catheter, through which the contrast agent and the saline solution can be injected into the patient during the imaging process.

The electric motors are connected via shielded electric cables to a battery which is located inside the room. The electric motors are in particular controlled by an injection monitoring unit arranged in the room, which is connected to a transmitting and receiving device located in the shielded room. The superior control and monitoring unit is connected to a further transmitting and receiving device located outside the room. Via the two transmitting and receiving devices, the control and monitoring unit controls and monitors the injection monitoring unit.

One disadvantage of such a system is that, due to the battery, the transmitting and receiving device and in particular the two electric motors and the injection monitoring unit, possible sources of electromagnetic fields are present which could reduce the quality of the MRI image. In order to avoid these potential sources of interference, therefore, electrically non-conductive materials are used and complicated shielding of all the aforementioned objects and their supply lines and connecting lines is carried out. Moreover, for the reasons mentioned above, a sufficient minimum distance of the objects from the magnet must be maintained at all times during the imaging process, which is associated with a certain risk of imperfect images in the event of the specialist personnel inadvertently not providing this minimum distance. Another disadvantage is the weight of the objects, in particular of the battery, and the space requirement thereof. In view of the high costs of shielding the room, the space required for the known system is very expensive. Finally, another disadvantage is the fact that rapid and unhindered access to the patient and/or magnet in the known system is made difficult due to the presence of tripod or carriage structures on which the known system is partially installed, and due to cables running across the floor.

SUMMARY OF THE INVENTION

The object of the invention is to minimise or entirely overcome all of the disadvantages described above.

The object of the invention is achieved by a hydraulic drive device, the at least one hydraulic line of which is guided to a pressure generating unit.

Due to the use of hydraulic components in the invention, assemblies used to date such as the battery, electric motors, power cable, injection monitoring unit and the two transmitting and receiving devices inside the room are no longer required. In particular, due to the use of the injection system according to the invention, no undesirable electromagnetic fields are produced since no power and no conductive material has to be used inside the room for the injection system. It is also advantageous that the injection device, in comparison to known injection devices, can be placed directly next to the patient and can even be moved into the MRI tube without adversely affecting the imaging results. As a result, the length of the hose via which the contrast agent is supplied from the injection device to the injection needle can be reduced to an easy-to-handle minimum. Since short hoses can be used, it is possible in particular to make a saving in terms of contrast agent, which must be present without bubbles in the hoses prior to injection. As a result, a considerable reduction in costs can be achieved, and above all patient safety can be further increased due to the fact that it is easier to check the shorter hose connections to ensure they are free of bubbles.

Therefore, while according to the invention it is possible in principle to arrange the pressure generating unit either inside or outside the room, placing it outside the room offers particularly good possibilities for avoiding electromagnetic interference effects. If the pressure generating unit is arranged inside the room, it should preferably be located at the greatest possible distance away from the imaging system, for example in a corner of the room at a distance of approx. 3 to 5 m away from the imaging system (e.g. MRI tube).

According to the invention, the hydraulic lines guided out of the room to a pressure generating unit and the hydraulic fluid guided in said lines simultaneously serve as a direct or indirect drive means for a conveying element and as an information carrier, in that hydraulic parameters such as pressure, change in pressure, throughflow and other parameters, such as displacement of the hydraulic fluid within the lines and the units connected thereto, can be transmitted from the hydraulic fluid itself to the pressure generating unit and at the latter can be measured outside the room either directly or indirectly, in a manner known per se. The passing of the hydraulic lines through the shielding of the room is important, since outside thereof no particular requirements can be placed on the magnetic properties of any further components of the drive device, in particular the pressure generating unit. Of course, the positive properties of the hydraulic system can in principle also be transferred to a pneumatic system, in which pneumatic instead of hydraulic operating means are used.

Since, when using hydraulic lines, the position and potential of electromagnetic fields need not be taken into account, it is also advantageous to use hydraulic lines in other similarly sensitive medical technical systems. By way of example, in the case of a nuclear spin tomography device, the hydraulic line can easily be integrated in a shaft of the MRI device.

In a further development of the invention, it is proposed that the pressure generating unit is integrated in the control and monitoring unit, in order to reduce the space requirement and save on double assemblies, such as those used to generate the operating voltage. It is also readily possible to use an electric motor as the drive for the pressure generating unit arranged outside the room, without having to provide special shielding of this electric motor.

It is further proposed that the injection system inside the room consists of essentially electrically non-conductive material, in order not to generate any sources of electromagnetic interference inside the room. Another advantage is achieved by deliberately omitting active components of the injection system in the vicinity of the imaging field, along with the associated elimination of risks such as artificial magnetic or electric interference fields which could adversely affect the imaging result. Direct risks from elements of the system that are accelerated by magnetic attraction are completely avoided if these elements are placed outside the room, since no element of the injection system inside the room has to be magnetised.

Another advantageous further development of the invention consists in that at least part of the hydraulic lines run in a concealed manner inside the room, in and/or on the floor, the wall and/or the ceiling, in order thus to allow the specialist personnel to enter the shielded room in a safe and flexible manner when working with the medical technical system, in particular with the MRI system.

Another further development of the invention may consist in that the hydraulic lines are filled with medically compatible, i.e. biocompatible hydraulic fluid, in order to completely rule out the risk of skin irritation or other possible damage in the event of leakage from the lines and any contact of the hydraulic fluid with the patient.

The invention can also advantageously be further developed in that the hydraulic fluid is present in the hydraulic lines under a resting pressure of 0.5 to 2 bar. By continually monitoring the pressure inside or outside the pressure generating unit, it can be ensured that a pressure drop caused by a leakage can be detected immediately. This could be used for example to immediately switch off the entire infusion system for safety reasons.

Another embodiment of the invention provides that a pressure transducer can be supplied by two pressure generating units, each of which is connected to a drive. Here, the control and simultaneous measurement of the respective drive parameters of one drive can be used to monitor the respective other drive, since the pressure converted by the pressure transducer directly determines the state of a drive of the other drive, and vice versa. For example, if the drive is configured as an electric motor, the state of the other motor can be determined via a current measurement of the motor, which is almost linearly proportional to the force required to apply the hydraulic pressure, with simultaneous direct measurement of the pressure in the hydraulic line, if the current is also measured and evaluated in the latter. Here the drives may even work in opposition, wherein then of course a certain power difference between the two drives would be necessary for injection purposes.

Another advantage is the fact that the pressure transducer comprises a piston/cylinder unit with two working chambers which are separated from one another by a piston coupled to the driven element. The hydraulic principle of the double-acting piston, which is known in principle, can thus also be used in an energy-efficient, cost-effective and easily controllable manner in the medical technical sector.

Unlike known injection devices which are placed on tripods or the like and require a considerable amount of space, the very light drive device according to the invention can be fixed directly to the MRI tube, which can usually hold only a little weight, in particular by means of a simple Velcro strip.

One advantage of a drive device according to the invention is the fact that it can easily be locked mechanically, for example by means of latching rods, threaded rods or other mechanical embodiments known in principle. For safety reasons, the injection system can in this simple manner be stopped very quickly.

The method for injecting liquid into a patient during MRI imaging by an MRI system is also advantageous due to the use of hydraulic parameters such as pressure, change in pressure per unit time, throughflow, volume of liquid, etc. as monitoring and control parameters, since the hydraulic transmission of information to outside means that there is no longer any need for complex electronic monitoring inside the room.

It is also advantageous that the pressure generating unit can be controlled by a control signal of a remote control which is located in the room, wherein the remote control transmits control signals in a unidirectional manner and a receiving unit inside the room receives the control signals and feeds them via a supply line into the electrical network, since such devices can be produced in a relatively cost-effective manner. In this case, it is preferably provided that the control signals are infrared signals and transmission takes place through a window of the room or by modulation of the control signals to a network frequency by the receiving unit, which can be inserted into a socket.

According to another embodiment of the injection system, it is provided according to the invention that the pressure generating unit is a hydraulic pump or the pressure generating device contains a hydraulic pump. In this way, a single pressure generating unit can be used for a plurality of pressure transducers, wherein the pressurised hydraulic fluid is allocated to the individual pressure transducers as necessary.

The allocation of the respectively required volume flow of hydraulic fluid to the individual pressure transducers takes place in a particularly advantageous manner via a respective proportional valve which establishes a connection between the pressure side of the hydraulic pump and the respective pressure transducer. It is particularly advantageous if the proportional valve is connected to both working chambers of the associated pressure transducer. In this way, forward and backward movements of the piston of the respective pressure transducer can be controlled by means of the same proportional valve.

In the hydraulic system which is used, there should also be a pressure accumulator arranged on the pressure side of the hydraulic pump and also a pressure sensor, by means of which the pressure on the pressure side of the hydraulic pump can be measured and the hydraulic pump can be switched off in the event of exceeding an upper limit and switched on in the event of falling below a lower limit. In this way, there is always a certain pressure reserve in the hydraulic system, so that even when the pump is idle the adjusting movement of the piston of the pressure transducer can start immediately. As soon as a sufficiently large pressure drop occurs in the hydraulic system, the pump starts to convey fluid, until the upper limit is again reached.

The position of the piston of the pressure transducer should preferably be able to be detected by means of a distance sensor assigned thereto, preferably a potentiometer. This distance detection is important for controlling and monitoring the respective injection parameters.

In order to prevent the piston of a pressure transducer when stationary from being inadvertently moved by means of external forces, the piston of this pressure transducer should be able to be acted upon by pressure from both sides at the same time in such a way that the piston remains at rest. With such a pressure control system, the precise desired rest position is always ensured regardless of any external forces acting on the piston.

In medical technical systems comprising hydraulic components, the aspect of ventilating the hydraulic system in particular represents a not inconsiderable problem. In order to solve this, it is proposed according to the invention that the surfaces of the piston assigned to the working chambers of each piston/cylinder unit are of different size, and there is a bypass cross section, preferably within the piston, through which a small leakage flow always flows in the event of a pressure difference between the working chambers. According to the invention, a small leakage flow is thus deliberately provided through the piston/cylinder units in order to achieve a continuous circulation of the hydraulic fluid. It will be understood that the bypass cross section need only be made large enough that a sufficient build-up of pressure is still possible over the piston to generate the necessary displacement forces. The leakage flow is therefore at most a few percent of the volume flow which is provided when the piston is displaced at maximum speed.

Due to the continuous circulation of hydraulic fluid, i.e. circulation in a loop, the fluid also reaches the hydraulic tank. According to the invention, it is further proposed that a surface of the hydraulic fluid in the hydraulic container is acted upon by a negative pressure, preferably a vacuum, which is generated and/or continuously maintained by means of a negative pressure pump. The air bubbles and gas bubbles reaching the hydraulic container are in this way absorbed by the negative pressure and conveyed out of the system by the negative pressure pump.

In addition to this continuous ventilation function, it is sometimes also desirable to achieve rapid removal of any gas bubbles by means of a large volume flow guided in a loop. For this purpose, it is provided that, in a ventilation position of the piston of the piston/cylinder unit, which is preferably a dead centre position, there is a ventilation bypass cross section which is larger than the bypass cross section, wherein the ventilation bypass cross section is preferably formed by a widening of the cross section of the cylinder of the piston/cylinder unit. As long as the piston is in the ventilation position, therefore, a large volume flow is set up in the loop and in this way leads to rapid removal of the gas bubbles from the system and transportation into the hydraulic container. For operation of the piston/cylinder unit, the large ventilation bypass cross section is not critical since, during the ventilation, no forces have to be applied via the driven element. However, the ventilation bypass cross section must be limited such that, with freedom of the driven element to external forces, at least the ventilation position can be left again in order automatically to re-close the ventilation bypass cross section, so that correspondingly large forces can again be generated via sufficient pressure differences over the piston.

According to one embodiment of the invention, it is proposed that the widening of the cross section of the cylinder in the ventilation position is designed in the form of a recess and/or channel which is located in the inner cylindrical surface of the cylinder and bridges over the axial length of the piston.

According to the invention, a method for injecting liquid into a patient during MRI imaging by an MRI system, wherein liquid is injected into a patient by displacing a conveying element by means of a drive device, is characterised by a hydraulic drive device which is acted upon by pressure via hydraulic lines from inside or outside the room.

In order to prevent inadvertent displacement of the piston of a pressure transducer when the latter is idle, it is provided that during these times the piston is set to the respective stationary position in order thus to make it insensitive to displacements by external forces. Here, the control parameter used is preferably the piston travel, which is detected via a distance sensor. The adjusting parameters used are advantageously the pressures acting in the two working chambers, wherein these two pressures are always kept above a certain minimum pressure.

Moreover, the pressures in all the hydraulic lines of the system according to the invention are always kept above a certain minimum pressure, even at times when the respective piston is stationary, in order to be able to quickly determine any leaks.

According to the invention, a hydraulic line can also be used as a control line for actuating specific functions of the injection process. This can advantageously be provided for a start function for dispensing the liquid to the patient, a stop function for stopping the injection system, a filling function for the uptake of liquid by the conveying element and/or a ventilation function for ventilating the conveying element, in that signals are generated for example by mechanical signal transmitters in order to be converted outside the room in a manner depending on the function.

In order to permit simple and reliable ventilation of the hydraulic system which is used, it is proposed according to the invention that a certain small volume flow is continuously maintained by a bypass cross section through the piston/cylinder unit, which volume flow is returned to the hydraulic container in which a surface of the hydraulic fluid is acted upon by a negative pressure, preferably by means of a negative pressure pump. In order to allow particularly rapid ventilation, it is provided that the volume flow in a particular position of the piston of the piston/cylinder unit is increased, so that faster circulation of the hydraulic fluid and faster removal of any gas bubbles temporarily takes place.

BRIEF DESCRIPTION OF THE DRAWINGS

The invention will be explained in more detail below with reference to an example of embodiment, in which.

DETAILED DESCRIPTION OF THE INVENTION

Figure 1:
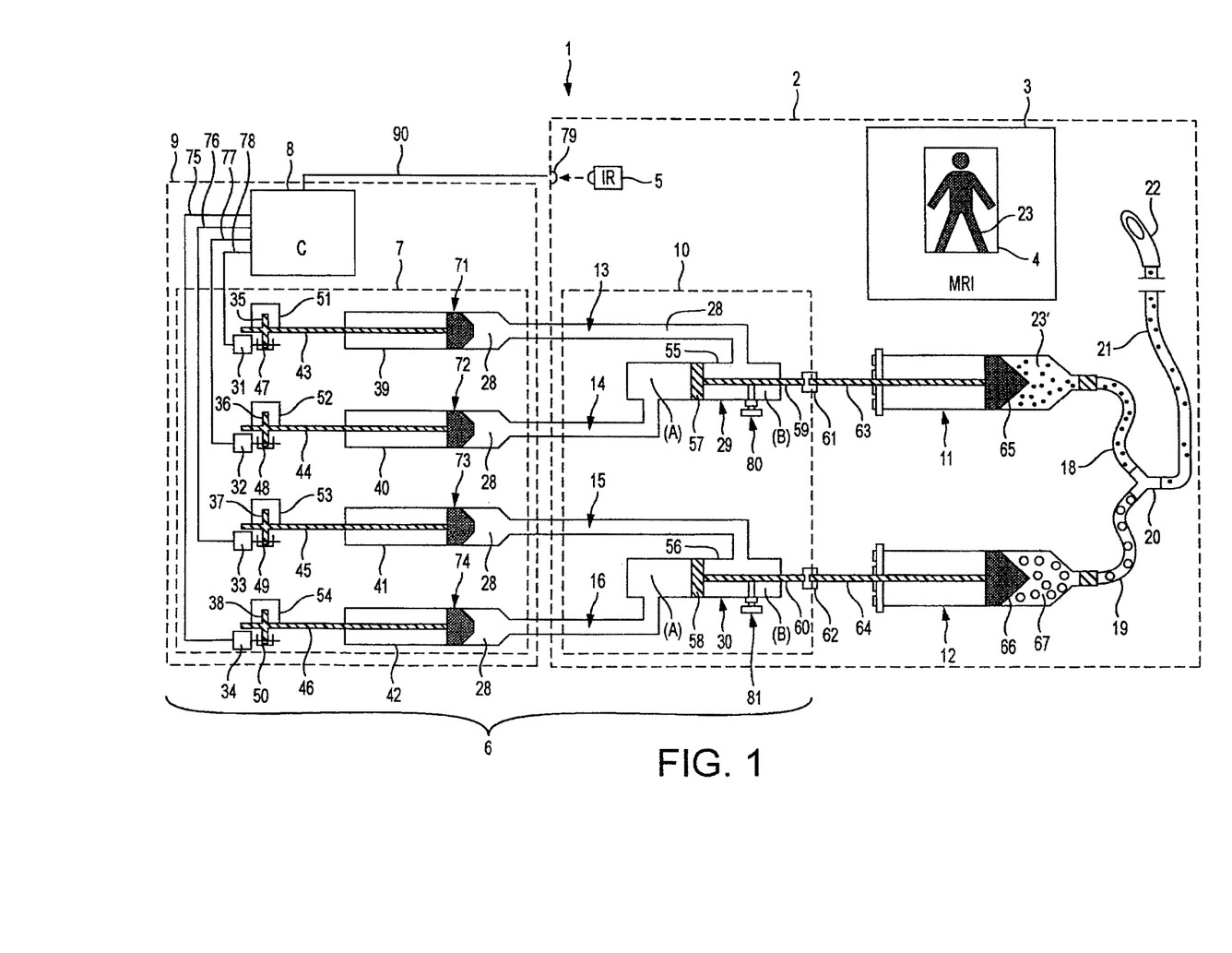
FIG. 1 shows a schematic view of a first embodiment of an injection system in conjunction with an MRI system.

An injection system 1 shown in FIG. 1 is arranged inside and outside a room 2 which is shielded from electromagnetic fields. Also located in the room 2 is the MRI device 3 in the form of a tube, in which a patient bed 4 is mounted such that it can be moved in and out. The injection system 1 comprises a remote control 5 located inside the room 2, from which control signals can be transmitted for controlling an injection device 6. The injection device 6 also comprises four pressure generating units 71, 72, 73, 74 which are arranged outside the room 2 and are combined to form a pressure generating device 7, and a control and monitoring unit 8, wherein these units are combined and connected to one another within a housing 9. Inside the room 2, the injection device 6 comprises a drive device 10 and two conveying elements 11, 12 connected thereto in the form of cylinder/piston units, in particular syringes. The injection device also includes the hydraulic lines 13, 14, 15, 16 which connect the drive device 10 and the pressure generating units 71, 72, 73, 74 through the shielding of the room 2. The drive device 10, the pressure generating unit 7, the control and monitoring unit 8 and the hydraulic lines 13, 14, 15, 16 form the injection device 6.

The two conveying elements 11, 12 are connected to a Y-shaped element 20 via hoses 18, 19. By means of a further hose connection 21, the Y-shaped element 20 can be connected to an injection needle 22 which is placed in a patient 23 for administering contrast agent 23' during an MRI examination.

The aforementioned devices and elements will be explained below in more detail.

The pressure generating units 71, 72, 73, 74 convey hydraulic fluid 28 into and out of the drive device 10 located in the room 2. Here, in each case two pressure generating units are connected by a respective hydraulic line 13, 14, 15, 16 to two pressure transducers 29, 30 of the drive device 10. The pressure generating units 71, 72, 73, 74 of the pressure generating device 7 in each case consist of a drive 31, 32, 33, 34 in the form of an electric motor, which drives a spindle 35, 36, 37, 38, and a cylinder/piston unit 39, 40, 41, 42, to the end of which a respective hydraulic line 13, 14, 15, 16 is connected. The cylinder/piston unit 39, 40, 41, 42 consists of the cylinder and a piston which can be displaced in a linear manner therein and which is connected to a threaded piston rod 43, 44, 45, 46. The piston rod 43, 44, 45, 46—and thus the piston—is furthermore protected against rotation in that a spring (not shown here) of the cylinder engages in a groove (likewise not shown) of the piston rod 43, 44, 45, 46. The drive 31, 32, 33, 34 and the cylinder/piston unit 39, 40, 41, 42 are connected in that the spindle 35, 36, 37, 38 is screwed by its internal thread onto the piston rod 43, 44, 45, 46. By means of an outer toothing on the spindle 35, 36, 37, 38, the electric motor can engage in the spindle 35, 36, 37, 38 by means of a toothed wheel 47, 48, 49, 50 connected to its shaft, and can rotate said spindle. As a result of the rotation of the spindle 35, 36, 37, 38, the piston rod 43, 44, 45, 46 and thus the piston undergo a lateral movement in the cylinder. Due to a retaining element 51, 52, 53, 54, the spindle 35, 36, 37, 38 furthermore cannot move in the lateral direction. The axes of rotation of the spindle 35, 36, 37, 38, of the toothed wheel 47, 48, 49, 50 and of the shaft moreover point in the same lateral direction as the direction of displacement of the piston rod 43, 44, 45, 46.

The drive device 10 consists of two pressure transducers 29, 30. A pressure transducer 29, 30 consists of a cylinder/piston element 55, 56 with a laterally movable piston 57, 58 and a driven element 59, 60 in the form of a piston rod which is connected thereto and is guided outwards. Between the piston 57, 58 and the end sides of the cylinder/piston element 55, 56, there are two working chambers A, B which are separated by the piston and are connected by hydraulic connections to the hydraulic lines 13, 14, 15, 16. Hydraulic fluid 28 which is under a pressure of approximately 0.5 to 2 bar is located in each case in the two chambers A, B, in the hydraulic lines 13, 14, 15, 16 and in the cylinder chambers of the pressure generating units 71, 72, 73, 74.

A latching element 61, 62 engages at the free end of the piston rod. The latching element is connected to a piston rod 63, 64 of the conveying unit 11, 12 in the form of a cylinder/piston unit, in particular a syringe. Connected to the piston rod 63, 64 is a piston 65, 66 which can be displaced within the syringe. One syringe is used to take up and dispense saline solution 67, while the other syringe takes up and dispenses the contrast agent 23'.

The electric motors of the pressure generating unit 7 are supplied with power from the control and monitoring unit 8 via connection lines 75, 76, 77, 78. Sensor data from sensors (not shown here) are also supplied to the control and monitoring unit 8. The sensors measure the pressure in all the hydraulic lines 13, 14, 15, 16, the position of the piston rods 43, 44, 45, 46 of the cylinder/piston units 39, 40, 41, 42, the temperature of the motors, the temperature of the hydraulic fluid 28 and/or the expansion of sections of the hydraulic lines 13, 14, 15, 16. The sensors are thus primarily assigned to the pressure generating unit 7 and are installed within the latter. It is not necessary to install the sensors inside the room 2, since all the aforementioned parameters can also be determined outside the room.

Using suitable evaluation software of the control and monitoring unit 8, the injection system 1 is kept ready for operation, that is to say essentially the motor currents of the electric motors are kept within the required ranges. An intervention on the control and monitoring procedure of the injection system 1 is therefore possible at any time by an operator outside the room 2 by means of suitable input means, such as a PC keyboard (not shown here). It is also possible that a further operator located inside the room 2 controls the injection system 1 via the control and monitoring unit 8 by means of the remote control 5. The infrared signal which is transmitted by the remote control 5 can be received by means of a receiving unit 79 in the form of an infrared receiver which is arranged inside the room, and can be modulated to the local network voltage. The receiving unit 79 is inserted into a socket inside the room 2. The network voltage, which is necessary in any case to operate the control and monitoring unit 8 and which is supplied to the latter via a supply line 90, can be decoded by the control and monitoring unit 8 so that the signals of the remote control 5 can ultimately be further processed by the software of the control and monitoring unit 8.

The second operator also has inside the room the possibility of mechanically intervening directly in the injection process, by actuating a mechanical lock 80, 81 in the form of a latching element which is provided on the pressure transducer 29, 30. When actuated, the latching element engages in particular in the respective driven element 59, 60 in the form of the piston rod, which for this purpose is provided with a toothing in some sections and prevents the further dispensing of contrast agent 23' or saline solution 67 by the injection device 6.

The dispensing or uptake of liquid by the conveying elements 11, 12 is determined exclusively by the pressure ratio between the two working chambers A, B of the pressure generating units 29, 30.

Figure 2:
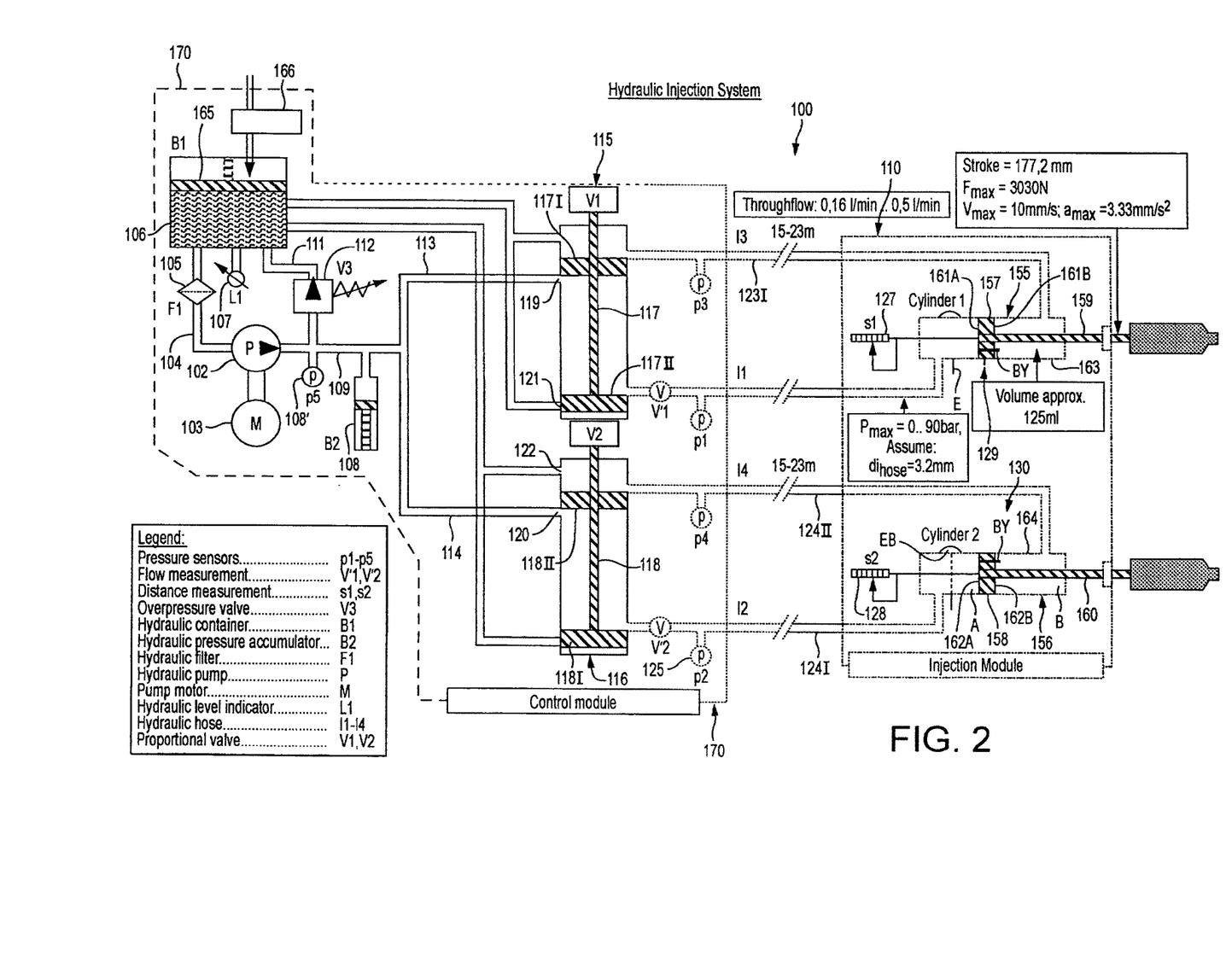
FIG. 2 shows a schematic view of a second embodiment of an injection system in conjunction with an MRI system.

FIG. 2 shows an alternative injection system 100 in which, instead of piston/cylinder units for generating pressure for the entire system, a single hydraulic pump 102 is provided which is driven by a motor 103. The drive device 110, which again consists of two cylinder/piston units 155, 156, is in principle unchanged compared to the system shown in FIG. 1. The two conveying elements in the form of syringes for injecting a contrast agent on the one hand and a saline solution on the other hand are not shown in FIG. 2 but are also present in this variant of the injection system 100. The patient bed and the patient himself, located for example within the tubular magnet of the MRI system, are also not shown.

Via a suction line 104, the hydraulic pump 102 sucks hydraulic fluid through a hydraulic filter 105 from a hydraulic container 106 in which the hydraulic fluid is under a positive pressure compared to atmospheric pressure. A filling level sensor 107 detects the level of the hydraulic fluid in the hydraulic container 106.

On the pressure side of the hydraulic pump 102, there is on the one hand a pressure accumulator 108 which ensures that always a certain volume of pressurised hydraulic fluid can be removed on the pressure side, even when the hydraulic pump 102 is idle. A pressure sensor 108' continuously detects the pressure and ensures that the control and monitoring unit (not shown) receives a switch-on signal in the event of falling below a lower limit and a switch-off signal in the event of exceeding an upper limit. On the other hand, branching off from the pressure line 109 is also a line 111 which leads back to the hydraulic container 106 and in which an adjustable positive pressure valve 112 is located.

The pressure line 109 splits into two lines 113 and 114 which each lead to a proportional valve 115, 116, by means of which the hydraulic fluid is allocated to the two working chambers A, B of the two piston/cylinder units 155 and 156.

The two proportional valves 115, 116 in each case have a piston rod 117, 118, on which there are in each case two pistons 117 I, 117 II and 118 I, 118 II at a distance from one another. Each of the proportional valves 115, 116 is provided with a central connection 119, 120 for the pressurised hydraulic fluid, and two connections 121, 122 arranged close to the end sides which are in each case connected via lines to the hydraulic container 106.

In each case two lines 123 I, 123 II and 124 I, 124 II lead from the opposite side of the proportional valves 115, 116, which lines lead to the working chambers A and B, respectively, of the piston/cylinder units 155, 156. In each of these lines 123 I, 123 II and 124 I, 124 II there is a respective pressure sensor 125, and there is a volume flow meter 126 in the lines 123 II and 124 I.

Depending on the position of the piston rods 117, 118 and of the pistons 117 I, 117 II and 118 I, 118 II connected thereto, a greater or lesser volume flow in the direction of a working chamber A or B of the cylinder/piston units 155, 156 is enabled, along with a corresponding return flow from the respective other working chamber B or A to the proportional valve 115, 116.

The respective position of the piston 157, 158 of the piston/cylinder units 155, 156 and of the piston rods connected thereto in the form of the driven elements 159, 160 (which lead to the conveying elements (not shown) in the form of syringes) can be detected by means of the distance sensors 127, 128. Using a control algorithm, which is integrated in the control and monitoring device (not shown in detail in the drawing), the position of the pistons 157, 158 at times when the latter are to assume a rest position is kept unchanged in that, in the event of external forces being applied via the driven elements 159, 160, the pressures in the working chambers A and B are adjusted such that no change in position of the pistons 157, 158 occurs. The proportional valves 115, 116 are accordingly actuated by the control and monitoring device.

A first error prevention measure of the injection system 100 consists in that, by means of the volume flow meter 126 and the pressure sensors 125, it is possible to check whether, for a measured displacement of the pistons 157, 158, expected pressure and volume flow conditions are actually obtained in the respective lines 123 I, 123 II and 124 I, 124 II.

In the injection system 100 shown in FIG. 2, the pressure generating device 170 may be arranged either inside or outside the room in which the device having a high field strength, i.e. in the case of MRI systems in particular the magnet, is located. If the pressure generating unit 170 is located inside the room, it is preferably positioned as far away as possible from the magnet itself so that the only lines that now run in the region of greatest field strength are the hydraulic lines 123 I, 123 II and 124 I, 124 II, and in particular not the electrical lines which were previously needed to operate electrical components such as, for example, actuating motors for the mechanical actuation of the conveying elements.

In order to achieve simple and reliable ventilation of the hydraulic system, the surfaces 161A, 161B, 162A, 162B of the pistons 157, 158 of the piston/cylinder units 155, 156 are of different size. This is achieved by means of a different cross-sectional area of the piston rod 159 in the region of the two working chambers A, B. While the piston rod 159 has a larger cross section on the driven side, i.e. in the region of the working chamber B, it is designed with a smaller diameter in the region of the working chamber A, since here only the operation of reading the distance sensor 127, 128 has to take place.

Due to the different surfaces 161A compared to 161B and 162A compared to 162B, there must always be a certain pressure difference between the two working chambers A and B, even in the rest state of the piston 157, 158. There is now a bypass cross section B in the form of a small bore in each of the pistons 157, 158. A small volume flow always takes place through the bypass cross section B, which brings about looped circulation of the hydraulic fluid. Any gas bubbles present in the system are thus guided through the corresponding hydraulic lines to the hydraulic container 106.

The surface 165 of the hydraulic fluid is acted upon by a negative pressure by means of a negative pressure pump 166, so that gas bubbles leave the hydraulic fluid and are removed from the system by means of the negative pressure pump 166.

In order to allow rapid ventilation when necessary, in a ventilation position E of the piston 155, 156 a ventilation bypass cross section EB is provided in the inner cylindrical surface of the cylinder 163, 164. In the ventilation position E, which corresponds to the left dead centre position of the piston 157, 158, this ventilation bypass cross section brings about ventilation via a much larger volume flow compared to the bypass cross section B in the piston 157, 158. Also in the case of this "rapid ventilation", removal of any gas bubbles takes place via the negative pressure pump 166 which is connected to the hydraulic container 106.

LIST OF REFERENCES

| | |
|---|---|
| 1 | injection system |
| 2 | room |
| 3 | MRI device |
| 4 | patient bed |
| 5 | remote control |
| 6 | injection device |
| 7 | pressure generating device |
| 8 | control and monitoring unit |
| 9 | housing |
| 10 | drive device |
| 11, 12 | conveying element |
| 13, 14, 15, 16 | hydraulic line |
| 18, 19 | hose |
| 20 | Y-shaped element |
| 21 | hose connection |
| 22 | injection needle |
| 23 | patient |
| 23' | contrast agent |
| 28 | hydraulic fluid |
| 29, 30 | pressure transducer |
| 31, 32, 33, 34 | drive |
| 35, 36, 37, 38 | spindle |
| 39, 40, 41, 42 | cylinder/piston unit |
| 43, 44, 45, 46 | piston rod |
| 47, 48, 49, 50 | toothed wheel |
| 51, 52, 53, 54 | retaining element |
| 55, 56 | cylinder/piston element |
| 57, 58 | piston |
| 59, 60 | driven element |
| 61, 62 | latching element |
| 63, 64 | piston rod |
| 65, 66 | piston |
| 67 | saline solution |
| 71, 72, 73, 74 | pressure generating unit |
| 75, 76, 77, 78 | connection lines |
| 79 | receiving unit |
| 80, 81 | lock |
| 90 | supply line |
| 100 | injection system |
| 102 | hydraulic pump |
| 103 | motor |
| 104 | suction line |
| 105 | filter |
| 106 | hydraulic container |
| 107 | filling level sensor |
| 108 | pressure accumulator |
| 108' | pressure sensor |
| 109 | pressure line |
| 110 | drive device |
| 111 | line |
| 112 | positive pressure valve |
| 113, 114 | line |
| 115, 116 | proportional valve |
| 117, 118 | piston rod |
| 117I/II, 118I/II | piston |
| 119, 120 | connection |
| 121, 122 | connection |
| 123I/II, 124I/II | line |
| 125 | pressure sensor |
| 126 | volume flow meter |
| 127, 128 | distance sensors |
| 129, 130 | pressure transducer |
| 155, 156 | piston/cylinder unit |
| 157, 158 | piston |
| 159, 160 | drive element |
| 161A/B, 162A/B | surfaces |
| 163, 164 | cylinder |
| 165 | surface |
| 166 | negative pressure pump |
| B | bypass cross section |
| E | ventilation position |
| EB | ventilation bypass cross section |
| 170 | pressure generating device |

The invention claimed is:

1. Injection system for injecting liquids within a strong magnetic field, an alternating magnetic field and/or a high-frequency electric field, for use with a medical technical system, comprising:
   a) a room which is shielded from electromagnetic fields by means of a shield,
   b) an injection device, by means of which liquid to be injected can be dispensed to a patient,
   c) a drive device of the injection device, by means of which at least one conveying element can be displaced for injection purposes, wherein the drive device comprises a pressure transducer comprising a piston/cylinder unit with a first working chamber and a second working chamber which are separated from one another by a movable piston;
   d) a control and monitoring unit which is arranged outside the shielded room,
   e) a hydraulic drive device comprising at least one hydraulic line of which is guided out of the room to a pressure generating unit in the form of a hydraulic pump, and
   f) a distance sensor arranged in the shielded room and located in a region of one of the working chambers of the pressure transducer, by means of which a position of the piston of the associated pressure transducer can be directly detected.

2. Injection system according to claim 1, wherein the medical technical system comprises an MRI system.

3. Injection system according to claim 1, wherein the medical technical system comprises a computer tomography system.

4. Injection system according to claim 1, wherein the pressure generating unit or a pressure generating device is integrated in the control and monitoring unit.

5. Injection system according to claim 1, wherein, inside the room, the room consists of essentially magnetically and electrically non-conductive material.

6. Injection system according to claim 1, wherein at least part of the at least one hydraulic line runs in a concealed manner inside the room, in and/or on a floor, a wall and/or a ceiling of the room.

7. Injection system according to claim 1, wherein the at least one hydraulic line runs in or on a shaft of the medical technical system, wherein the shaft is guided out of the room.

8. Injection system according to claim 1, wherein the hydraulic lines are filled with biocompatible hydraulic fluid.

9. Injection system according to claim 1, wherein the hydraulic fluid is present in the hydraulic lines under a resting pressure of about 0.5 to 2 bar.

10. Injection system according to claim 1, wherein the hydraulic drive device can be fixed to the MRI system.

11. Injection system according to claim 1, wherein the drive device can be locked by means of a mechanical lock.

12. Injection system according to claim 1, wherein the pressure generating unit is controlled by a control signal of a remote control which is located in the room.

13. Injection system according to claim 12, wherein the remote control transmits control signals in a unidirectional manner and a receiving unit inside the room receives the control signals and feeds them via a supply line into an electrical network, from where the control signals can be read outside the room.

14. Injection system according to claim 13, wherein the control signals are infrared signals configured to be transmitted through a window of the room or by modulation of the control signals to a network frequency by the receiving unit, the receiving unit configured to be inserted into a socket connected to the supply line.

15. The injection system according to claim 1 wherein the system further comprises a volume flow meter and a pressure sensor, and wherein the control and monitoring device is configured to compare expected pressure and volume flow conditions for the piston position to actual pressure and volume flow conditions.

* * * * *